United States Patent
Wölfelschneider et al.

[11] Patent Number: 5,693,003
[45] Date of Patent: Dec. 2, 1997

[54] ENDOSCOPE AND METHOD FOR DETERMINING OBJECT DISTANCES

[75] Inventors: Harald Wölfelschneider; Gerhard Schmidtke, both of Freiburg; Peter Wilhelm, Maulbronn, all of Germany

[73] Assignee: Richard Wolf GmbH, Knittlingen, Germany

[21] Appl. No.: 551,215

[22] Filed: Oct. 31, 1995

[30] Foreign Application Priority Data

Nov. 3, 1994 [DE] Germany ............ 44 39 227.3

[51] Int. Cl.⁶ .................................................. A61B 1/07
[52] U.S. Cl. ........................................ 600/117; 600/170
[58] Field of Search ............................ 600/117, 118, 600/108, 170, 173, 182; 356/241, 4.07, 5.1, 5.15

[56] References Cited

U.S. PATENT DOCUMENTS

| | | | |
|---|---|---|---|
| 3,608,547 | 7/1968 | Sato | 600/117 |
| 3,744,906 | 7/1973 | Sato et al. | 600/117 |
| 4,292,961 | 10/1981 | Kawashima | 600/117 |
| 4,340,302 | 7/1982 | Oku | 600/117 |
| 4,633,855 | 1/1987 | Baba | 600/117 |
| 5,190,028 | 3/1993 | Lafferty et al. | 600/129 |
| 5,210,587 | 5/1993 | Ohmamyuda et al. | 356/5.15 |
| 5,430,537 | 7/1995 | Liessner et al. | 356/5.1 |

FOREIGN PATENT DOCUMENTS 1766904  5/1971  Germany.

*Primary Examiner*—Richard J. Apley
*Assistant Examiner*—John P. Leubecker
*Attorney, Agent, or Firm*—Panitch Schwarze Jacobs & Nadel, P.C.

[57] ABSTRACT

A measuring method for determining the distance between the distal end of an endoscope and an object to be examined uses an optical radar and an endoscope, which comprises a distance measuring device. For carring out the measuring, a transmitting fiber optic and a receiving fiber optic in the endoscope are guided separately to respective separate optic modules at the front end of the endoscope. A semiconductor laser feeds a high frequency amplitude-modulated light in the transmitting fiber optic, which is projected by the transmitting optic module on the object in the form of a light spot. The light reflected from the object is received by the receiving optic module and guided through the receiving fiber optic in the endoscope to a light detector of a control unit. In the control unit a phase measurement is carried out and an evaluation device computes the distance information from the phase difference.

9 Claims, 5 Drawing Sheets

ENDOSCOPE AND METHOD FOR DETERMINING OBJECT DISTANCES

BACKGROUND OF THE INVENTION

The invention relates to an endoscope and a method for determining the distance between an object and the distal end of the endoscope, comprising a light emitter for producing a transmitting light beam, a transmitting fiber optic for transfering the transmitting light beam to the distal end of the endoscope, a transmitting optic provided at the distal end of the transmitting fiber optic, situated at the distal end of the endoscope for projecting the emitting light beam onto the object, the axis of the transmitting optic being adjusted to the viewing direction of the endoscope, and means to detect the return scattering or reflected part from the object of the transmitting light beam projected on to it.

DESCRIPTION OF THE PRIOR ART

An endoscope of this type is known from the German patent 1766904. The principle of this endoscope consists of projecting a thin light beam from a projecting device, arranged at a certain lateral distance from the objective lens system of the endoscope, and producing an image of a light spot caused by the light beam on the object in a recording device for determining the position of the light spot within the visual field of the optical system. A further principle which is also described in the above mentioned patent, uses the triangulation method and two projection devices with two projected light spots produced on the object in the manner described above. One of the two projection devices can be moved using the control mounting, allowing the direction of one of the thin parallel light beams to be changed, in order to converge the light spot produced by this light beam on the surface of the object with the light spot produced by the beam in the fixed direction. By these means, the amount of adjustment of one projecting device relative to the other serves as a measure of the distance to the front end of the object.

Such object distance measurement has several disadvantages. Should one of the imaged positions of one light spot be used for recording the distance, then this can only then be carried out correctly when the object offers a substantially square face with regard to the optical axis of the endoscope objective. Should such a distance measuring device work according to the triangulation principle, then depending on the mechanics of the adjusting device, trimming and reading errors may occur. A quick succession of measurements, for example to detect the position of a moving object, cannot be carried out with such distance measuring devices.

SUMMARY OF THE INVENTION

The object of the present invention is to overcome the above mentioned disadvantages of known endoscope devices, and to construct an endoscope with a device for determining object distances from the distal end of the endoscope in such a way as to allow automatic error correction and a quick succession of measurements using purely optical and electronic means.

Such an endoscope, solving the above problems, is according to the invention, characterized in that the detecting means comprises a receiving optic, arranged directly next to the transmitting optic, and a receiving fibre optic, separate from the transmitting fiber optic, but guided with it through the endoscope to its proximal end, the receiving optic being adjusted to the viewing direction of the endoscope optic; the detecting means further comprising a light receiver connected to the proximal end of the receiving fibre optic and that there is a control unit connected to the light receiver and emitter for controlling the light emitter by means of an electric transmitting signal, said control unit producing an electrical receiving signal from the light received from the light receiver and determining the object distance by evaluating the dependence of the receiving signal on the transmitting signal. Further advantageous features of the endoscope according to the invention are specified in dependent claims 2 to 8.

One embodiment which works according to the principle of the optical radar is formed such that the light emitter comprises a laser diode for producing a high frequency amplitude-modulated transmitting light beam from the transmitting signal which is connected to the transmitting fiber optic, the control unit further comprising a phase monitor for comparing the phase position of a reference signal produced from the transmitting signal with the phase position of the receiving signal, for producing a phase signal and intensity signal, there being an evaluation device for producing and outputting an output signal according to the object distance.

The transmitting and receiving fiber optics are introduced into the endoscope in the proximity of the light connection, and run through the same lumen as the illumination fibers. Alternatively, a joint connection may be made, in which the illumination fibers and measuring fibers must be separated in the proximity of the light projector and measuring unit. The fibre optics can be made of glass or plastics and connect the optical measuring system of the endoscope with the electronic part of the distance measuring device. To this end, there are provided plug connections at the ends of the fibers and on the control unit.

The transmitting fiber optic part of the transmitting optic and the receiving fiber optic part of the receiving optic are at the distal end of the endoscope. The primary purpose of the transmitting optic is to collect the diverging irradiated light, whereas the receiving optic has the purpose of concentrating the return scattering and reflected light from the object. With the transmitting lumen the concentration is very tight, in order to obtain a high lateral definition i.e. a small light spot on a large object area give an almost point shaped measurement.

The aperture of the receiving optic is chosen to be larger than that of the transmitting object, ensuring that the transmitting light spot is always in the field of view of the receiving optic. The optical axes of the transmitting and receiving optic are offset and not parallel. By these means, the transmitting light spot changes its position in the receiving field of view, dependent on the object distance.

It is purposeful to connect an adjusting unit to the transmitting and receiving optics, by means of which the transmitting and receiving optics may be trimmed and adjusted with regard to each other. By these means, the measurement range determines that range in which the transmitting light spot lies almost completely in the field of view of the receiving optic. The trimming is carried out in two axes pependicular to the optical axis.

With a 90° offset beam path of the endoscope, the trimming is carried out on the one hand by tilting the emitting and receiving optics in a direction which lies in that plane formed by the original optical axis and the 90° offset, and on the other by rotation of the transmitting and receiving optics about the original optical axis. With a direct vision beam path the trimming is effected by tilting in two axes, which both lie perpendicular to each other and the optical axis.

The evaluation device comprises a microprocessor which linearises the intensity- and distance dependent phase signal, depending on the intensity of the received light ray, and on defined optical parameters. The microprocessor can further carry out a phase correction to compensate for deviations in climate and operating temperature.

The invention also concerns a method for determining object distances between the distal end of the endoscope and an object to be examined by means of an optical radar according to those features specified in claims 9 and 10.

BRIEF DESCRIPTION OF THE DRAWINGS

Further features of the endoscope and method according to the invention are hereinafter described with reference to the enclosed drawings by way of embodiments. These show.

DETAILED DESCRIPTION OF THE PREFERRED EMBODIMENTS

Figure 1:
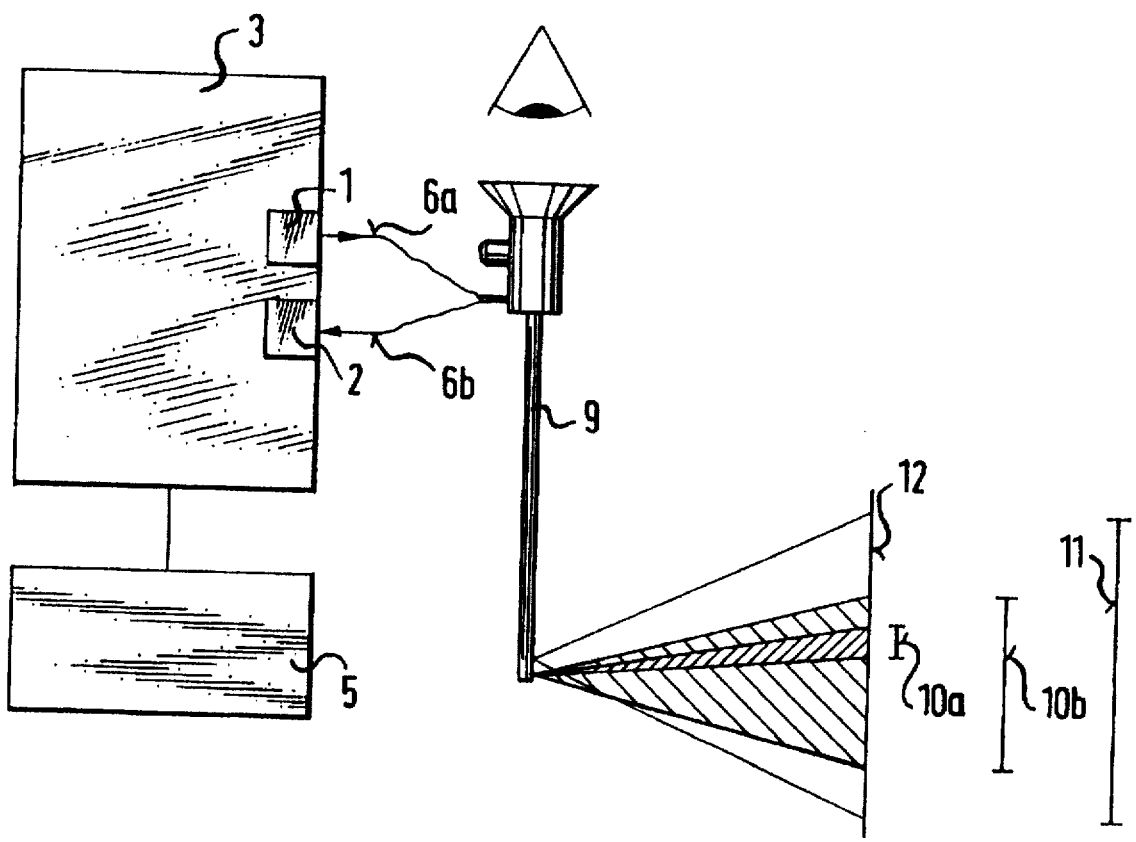
FIG. 1 schematically and in the form of a modular block diagram, the principle of an endoscope with a device for determining object distances from the distal end of the endoscope according to the invention, FIG. 2 the control unit and evaluation device shown in FIG. 1 in the form of a detailed block diagram, FIG. 3 a longitudinal cross-section through the distal end of the endoscope, FIG. 4 a longitudinal cross-section through the proximal part of the endoscope with one embodiment of the coupling and decoupling of the illumination and measuring fibers, FIG. 5 schematically, the distribution of field of view, the illumination and receiving aperture as well as the start of the measurement scale realized by the endoscope, FIG. 6 a plan view of the distal end of the endoscope, FIGS. 7A and 7B the principle of the function of the adjusting unit with a 90° offset beam path, FIGS. 8A and 8B the principle of the function of the adjusting unit with a direct vision beam path.

The endoscope shown in FIG. 1 comprises a 90° offset beam path with a 90° viewing direction. The transmitting (6a) and receiving (6b) fiber optics fed through the proximal end section of the endoscope (9) are respectively connected to the light emitter (1) and light receiver (2) which form part of control unit (3) represented as a block. The control unit (3) is connected to an evaluation device (5).

Figure 2:
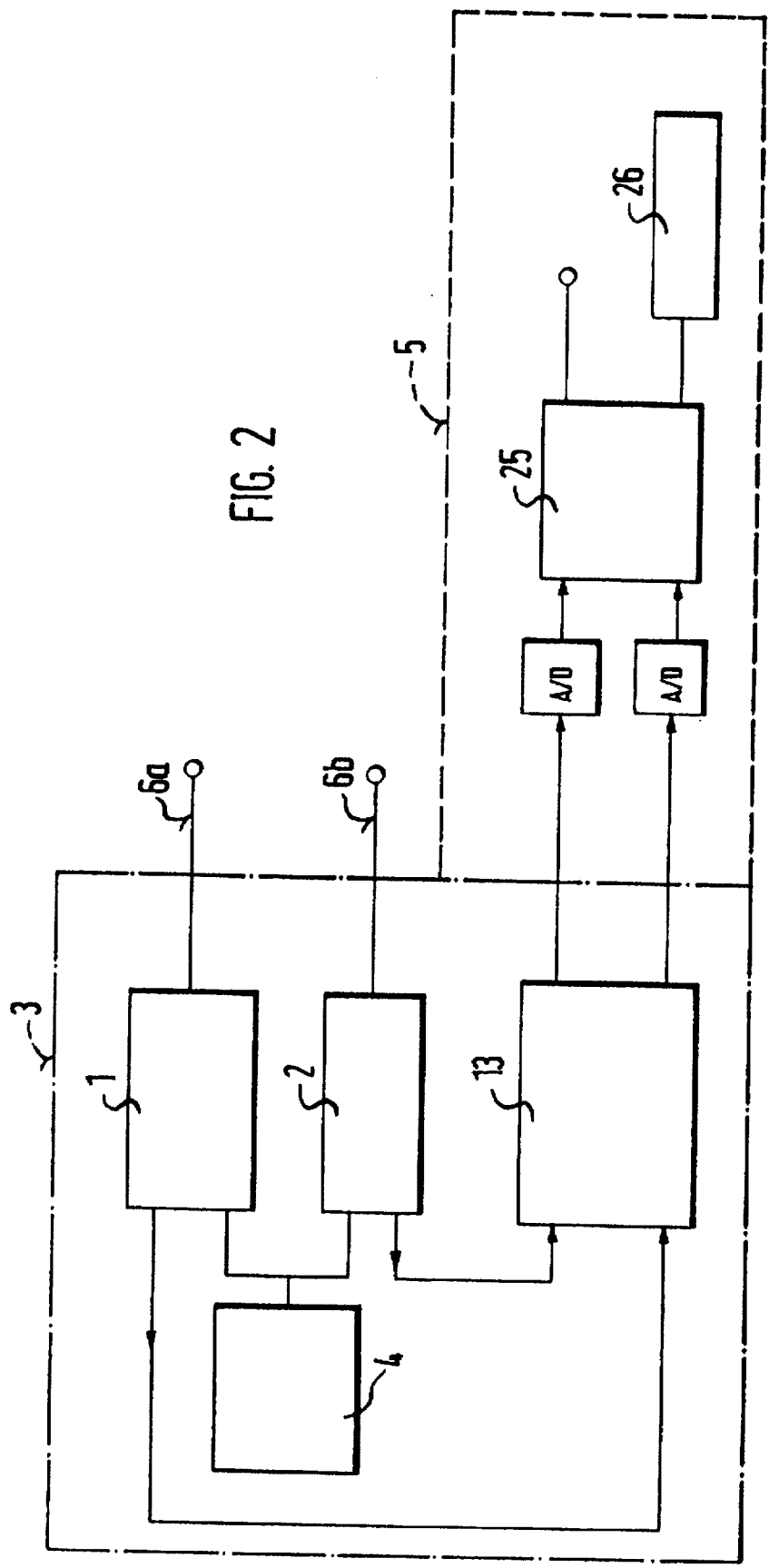

The control unit (3) and the evaluation device (5) are shown in detail in the detailed block diagram shown in FIG. 2. The control unit (3) comprises the light emitter (1), the light receiver (2), a local oscillator (4) and a phase monitor (13). Light from a high frequency amplitude-modulated laser diode is inputted from the light emitter (1) to the emitting fiber optic (6a). The receiver receives the measuring signal reflected from the object and connected from the receiving fiber optic (6b) and carries it to the phase monitor (13), after having been converted to IF (Intermediate Frequency). The phase monitor then supplies an electrical phase signal and an electrical intensity signal to an evaluation device (5) which comprises a microprocessor. The microprocessor (25) corrects (linearizes) the intensity and distance dependent phase signal by way of a correction multinomial:

$$d = p + a(p) \cdot i^2 + b(p) \cdot i + c(p)$$

in which d is the object distance, p the phase, i the object intensity and a,b and c are coefficients, depending on the type of optic. These coefficients can be stored in the PROM-memory of the microprocessor.

The microprocessor (25) further carries out phase corrections to compensate for deviations and changes in climate and operating temperature.

In an actual test carried out with an endoscope according to the present invention the following values are given: the modulation frequency of the light emitter: 160 MHz, the frequency of the local oscillator: 149.3 MHz, the frequency of the signals led to the phase monitor: 10.7 MHz.

The light emitter comprises a semiconductor laser diode, which is controlled by the optic module. The laser beam which is emitted has a wavelength of 830 nm. An adjustment of 50 Ohms to 3 Ohms occurs between the output of the modulation generator and the input to the laser diode.

In this manner the light intensity changes periodically (with 160 MHz) between approx. 0 mW and nearly 30 mW. The average power is approx. 12 mW.

The light receiver (2) contains an avalanche diode, with the help of which the optical receiving signal arriving via the receiving fiber optic (6b) is changed into an electrical signal. In order to better isolate the measuring signal from outside influences (radio waves), it is converted downwards from 160 MHz IF to 10.7 MHz by means of mixer circuit. The avalanche photodiode is biased at 230 V by a specically designed high voltage module (not shown in FIG. 2).

The phase monitor (13) receives both 10.7 MHz signals from the light emitter (1) and the light receiver (2). The phase indicator realized in the phase monitor (13) achieves a measuring range of 200 mm maximum, which corresponds to a phase shift af approx. 110°. An intermediate frequency amplifier (not shown) in the phase monitor (13) produces the intensity signal for the measuring signal for the extensive processing in the evaluation device (5).

Whilst using the endoscope, intensity changes of 1000:1 or more arise, depending on the photometric law of distance and various reflection characteristics of the object and surfaces of the target. No known amplifier, nor the photo detector in the light receiver (2) can process such a large range without phase errors. For this reason the phase signal delivered from the phase monitor (13) must be corrected on the basis of the intensity signal produced from said phase monitor in the evaluation device (5) for distance measurement by the correction multinomial cited above. The parameters a, b and c in the correction multinomial are to be defined for each type and for each particular application, and are stored in an EPROM memory of the microprocessor.

To make the management easier, the software of the microprocessor (25) may contain a multitude of functions for communication with a personal computer. A program running on the personal computer can evaluate the correction coefficients for several curve characteristics for various surfaces of the objects to be measured, and pass these back on to the microprocessor (25). The microprocessor (25) supplies a nominal voltage to an analog output, this nominal voltage allowing an automatic transducing with any X-Y recorder. A monitoring device (26) is connected to the microprocessor.

Figure 3:
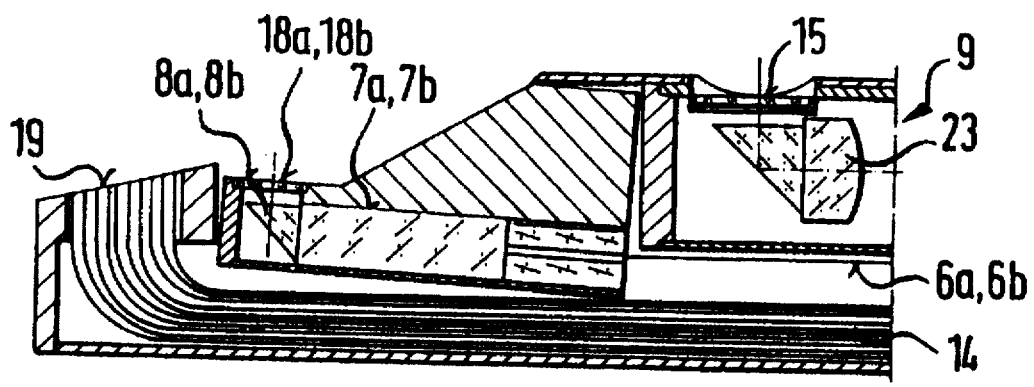

FIG. 3 illustrates an enlarged longitudinal section through the distal end of the endoscope according to the invention. The transmitting fiber optic (6a) and receiving fibre optic (6b) which are led through the endoscope tube in the same lumen as the illumination fibres (14), terminate respectively at the transmitting optic (7a) and receiving optic (7b) as an image giving system. By this means the transmitting optic module comprises the transmitting fiber optic (6a), the transmitting lens (7a) and a transmitting deflecting prism (8a), whilst the receiving optic module comprises the receiving fiber optic (6b) the receiving lens (7b) and the receiving deflecting prism (8b). Both optic modules are placed in trimming mounts which allow adjustment and trimming explained hereinafter by way of FIGS. 7a, 7b and 8a, 8b. There is further housed, at the distal end of the endoscope, an illumination window (19) at which the illumination fibers (14) end, an endoscope terminal window (15) and the objective (23) of the endoscope.

Figure 4:
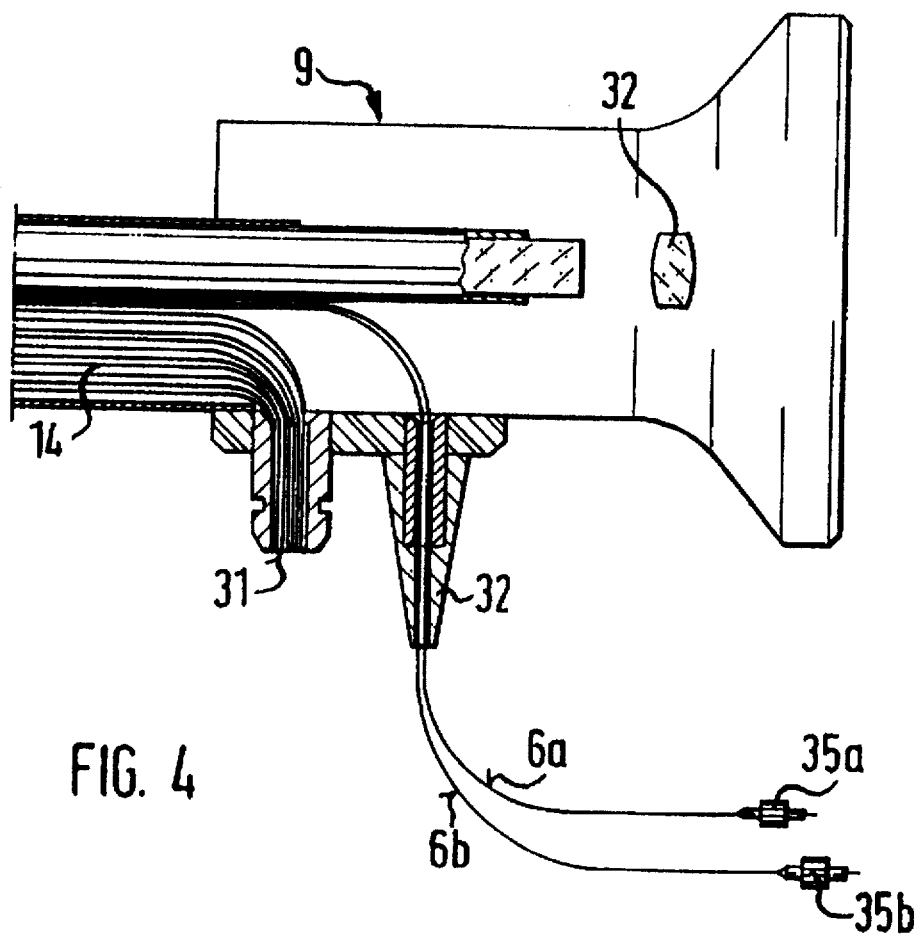

FIG. 4 shows the components at the proximal part of the endoscope (9) with the eyepiece (33). The illumination fibers (14) end at a separate connection (31), whereas the transmitting fiber optic (6a) and receiving fiber optic (6b), which are guided through the shank of the endoscope (9) in the same lumen as the illumination fibres (14), are lead through to a separate connection (32) ending at plug sockets (35a) and (35b) repectively, with which they are connected to the light emitter (1) and light receiver (2) in the control unit.

GRIN lenses may be used for those lenses (7a) and (7b) of the transmitting and receiving objects shown in the longitudinal cross section in FIG. 3, whereas the fiber optics may be made of glass or plastics material.

Figure 5:
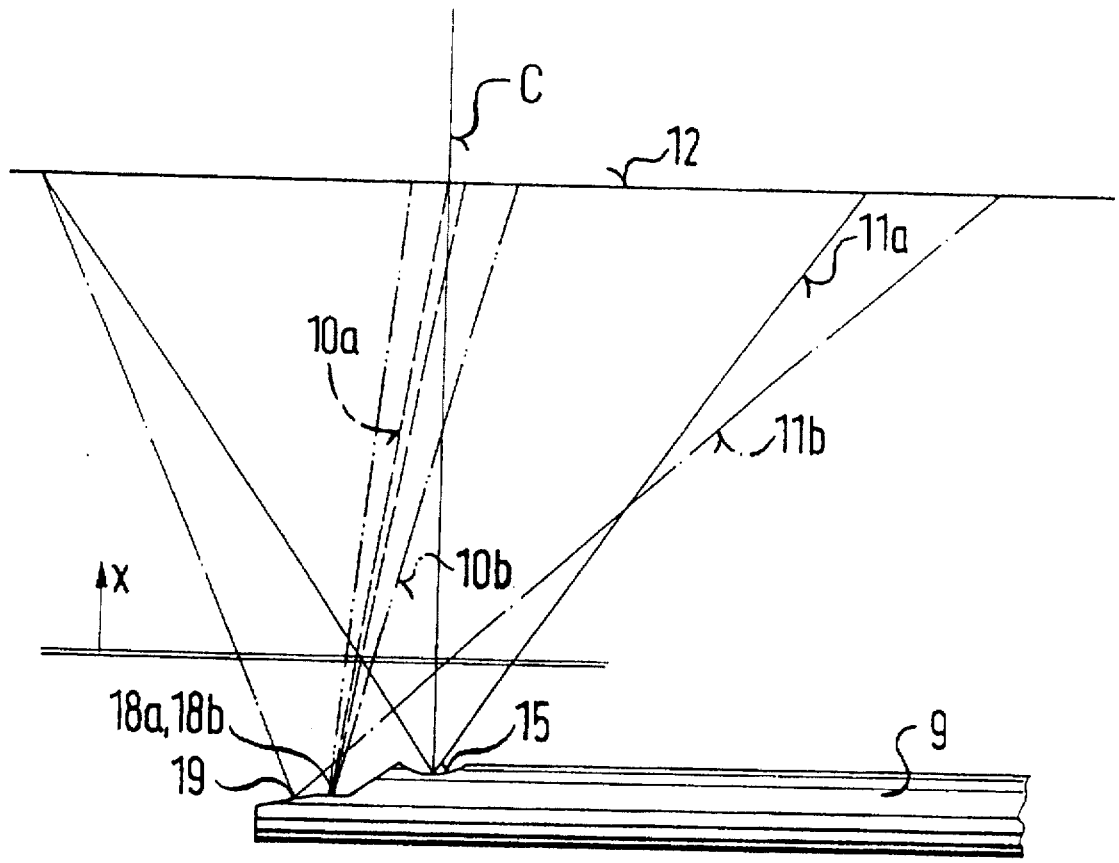

FIG. 5 shows the beam paths and the field of view. The outer contours (11b) of the illumination are represented by dot dash lines and the outer contours (11a) of the field of view of the endoscope are represented by full lines. The aperture (10b) of the receiving optic represented by the double dot dash line is chosen to be larger than the aperture (10a) of the transmitting optic represented by a dashed line, in order to ensure that the transmitting light spot is always completely in the field of view of the receiving optic.

Apart from concentrating the radiated and received light, the transmitting optic and receiving optic carry out, with for example a 90° offset beam path, the deflecting of the optical axes of the measuring beams according to the viewing direction of the endoscope, given by the axis C. This is accomplished by the previously mentioned refracting or reflecting prisms (8a) and (8b), connected to lenses (7a) and (7b).

The optical axes A, B of the transmitting and receiving optics are not parallel, but are offset to one another. With this, the transmitting light spot changes its position in the receiving field of view (10b) depending on the distance of the object surface (12) from the distal end of the endoscope (9). By trimming the transmitting and receiving optic to one another, the measuring range is defined as that range in which the transmitting light spot lies almost completely in the field of view of the receiving optic.

Figure 6:
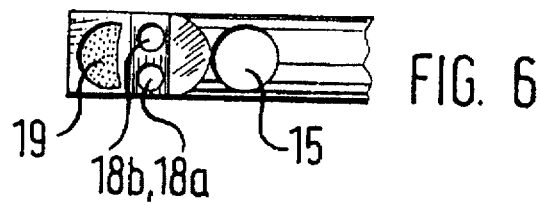

FIG. 6 shows, in a plan view of the distal end of the endoscope, the terminal window (15) for the optical system of the endoscope, under which the endoscope objective is positioned, the terminal window (18a) for the transmitting optic, under which the deflecting prism (8a) is situated, and separate from this, the terminal window (18b) for the receiving optic, under which the prism (8b) is situated, and the terminal window (19), at which the illumination fibres (14) terminate.

Figure 7B:
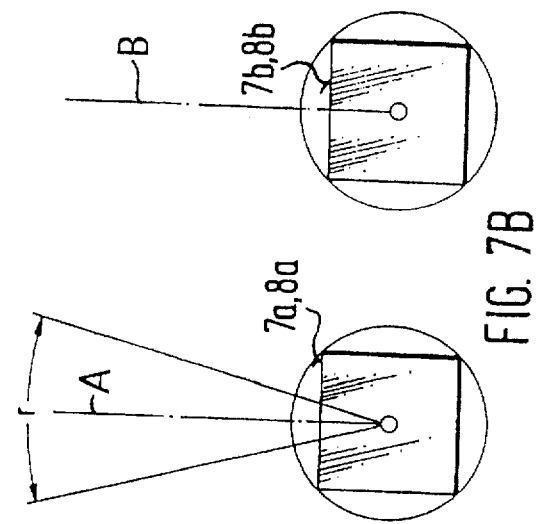
Figure 7A:
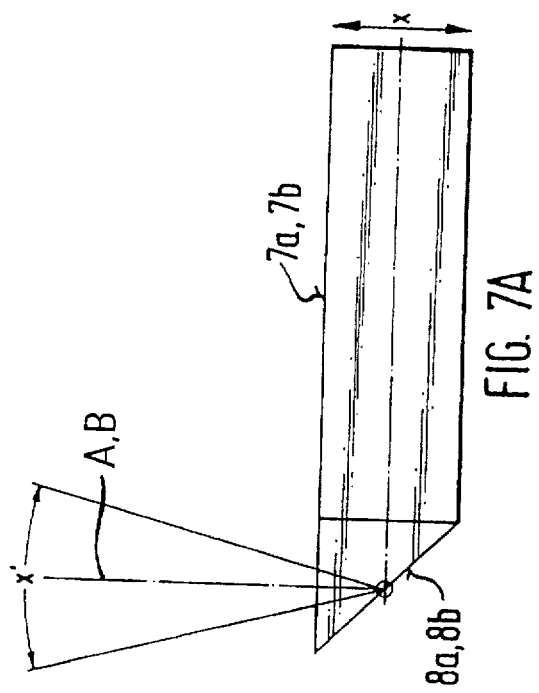

FIGS. 7A and 7B illustrate the trimming of the transmitting and receiving optics for an endoscope with a 90° offset beam path. The trimming is carried out by:
a) tilting the optic modules 7a, 8a as well as 7b,8b in the x-direction in that plane formed by the original optical axis (longitudinal axis of the endoscope) and the 90° offset axis (FIG. 7A), as well as
b) by rotation r of the optic module about the original optical axis (FIG. 7B).

Figure 8B:
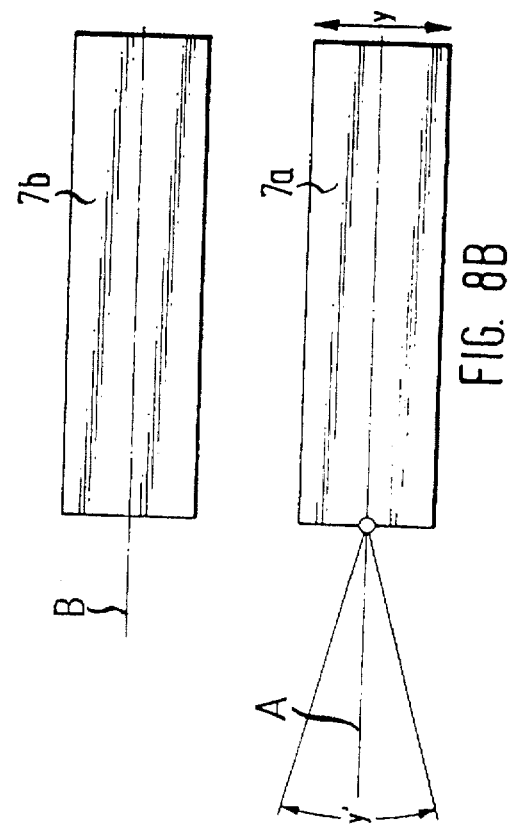
Figure 8A:
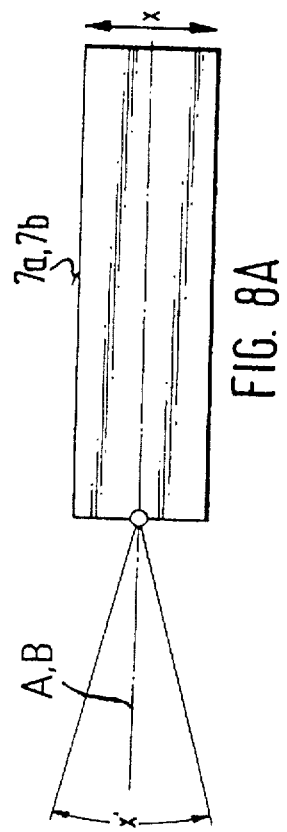

With an endoscope having a direct vision beam path, the trimming is illustrated in FIGS. 8A and 8B. The transmitting and receiving optics are tilted in two directions x' and y' which are at right angles to each other and orthogonal to the optical axis.

Instead of, or additionally to the trimming being carried out by the tilting of the transmitting and receiving optics as described above, with suitable adjusting units, the measuring beam may be so guided, allowing it to be continually scanned over the surface of the object.

The apparatus of the endoscope according to the invention must first be calibrated, as the allocation of the phase to the intensity depends on the working point of the laser diode positioned in the light emitter, and on the temperature. Such calibration can be updated as often as is required. For this, an object (12) is placed at a defined distance from the endoscope (9), and the phase and intensity are measured as indicated above. The microprocessor (25) contained in the evaluation device (5) then carries out the necessary offset correction. During the measuring, the distance object/endoscope is continually outputted.

The method of distance measurement using the help of the optical radar, known per se from telemetering technology, allows a measurement of the distance between the distal end of an endoscope or techoscope and the object with a rate of measurement essentially determined by the processing time in the digital evaluation device. This is smaller than 1/10 of a second and corresponds to real-time measuring and allows distance measurement of relatively fast moving objects.

In combination with the relative sizes of the object, recognized in the ocular of the endoscope, the measured value of distance can be used to ascertain the absolute sizes of the object. Moreover by way a of numerical method, the topology of objects, or parts of objects may be determined.

We claim:

1. An endoscope with a device for determining object distances from the distal end of the endoscope, comprising a light emitter (1) for producing a transmitting light beam (10a), a transmitting fiber optic (6a) for transferring the transmitting light beam (10a) from the proximal to the distal end of the endoscope (9), a transmitting optic (7a, 8a) having an optical axis (A) provided at the distal end of the transmitting fiber optic (6a) situated at the distal end of the endoscope for projecting the transmitting light beam (10a) in the form of a light spot onto the object, the optical axis (A) of the transmitting optic (7a, 8a) being adapted to a viewing direction of the endoscope, and means to detect a reflected part of the light spot of the transmitting light beam (10a) projected onto the object, characterized in that the detecting means comprises a separately arranged receiving optic (7b, 8b) having an optical axis (B), arranged directly next to the transmitting optic (7a, 8a) and a receiving fiber optic (6b), separate from the transmitting fiber optic (6a), and guided with it through the endoscope to its proximal end, the receiving optic (7b, 8b) being also adjusted to the viewing direction of the endoscope, the detecting means further comprising a light receiver connected to the proximal end of the receiving fiber optic (6b) and that there is a control unit (3, 5) connected to the light receiver (2) and emitter (1) for controlling the light emitter (1) be means of an electrical transmitting signal, said control unit (3, 5) producing an electrical receiving signal from the light received from the light receiver (2) and determining the object distance by evaluating the difference between the receiving signal and the transmitting signal, the device further including an adjusting unit connected to the transmitting optic (7a, 8a) and the receiving optic (7b, 8b) for making each of these separately adjustable in two directions which are perpendicular to one another.

2. An endoscope according to claim 1, characterized in that the light emitter (1) comprises a laser diode for producing a high frequency amplitude-modulated transmitting light beam from the transmitting signal, which is connected to the transmitting fiber optic, the control unit (3,5) further comprising a phase monitor (3) for comparing the phase position of a reference signal produced from the transmitting signal with the phase position of the receiving signal, this producing a phase signal and intensity signal, there being an evaluation device (5) for producing and outputting an output signal, according to the object distance.

3. An endoscope according to claim 2, characterized in that the evaluation device (5) comprises a microprocessor which carries out a linearization of intensity and distance dependent phase signals, and an offset correction to compensate for deviations in climate and operating temperature.

4. An endoscope according to claim 1 characterized in that the optical axes (A, B) of the transmitting and receiving optics (7a, 8a and 7b, 8b) are not parallel and form a small angle, whereby the reflected part from the object of the transmitting light spot changes its position in a field of view of the receiving optics, dependent on object distance.

5. An endoscope according claim 1 characterized in that the transmitting and receiving optics (7a,8a and 7b,8b) situated together at the distal end of the endoscope are similarly constructed and each comprising a GRIN lens (7a,7b) and a deflecting prism (8a,8b) for deflecting the beam path of the transmitting and receiving light beams respectively.

6. An endoscope according to claim 1 characterized in that the adjusting unit is arranged to rotate (direction r) the associated optical unit about an axis generally arranged in the longitudinal direction of the endoscope, and to tilt (direction x) said optical unit about a plane running through this axis.

7. An endoscope according to claim 1, characterized in that the adjusting unit is arranged for alternately adjusting the transmitting and receiving optics allowing a scanning of an object area by the transmitting and receiving light beams.

8. A method for determining the distance between the distal end of the endoscope having a field of view and an object to be examined by means of an optical radar, the endoscope comprising two separate optical fibers for carrying respectively a transmitting light beam to a transmitting optic and a receiving light beam from a receiving optic to a light receiver, and both optics being so arranged at the tip of the endoscope that the transmitting light spot on the object and the receiving field of view of the measuring range overlap and lie within the endoscopic field of view, characterized by the following steps:

producing a high frequency amplitude-modulated transmitting light beam and projecting this on an object to be examined in the form of a light spot by means of the transmitting optic, receiving a reflected part of the transmitting light beam from the object using the receiving optic and leading the reflected part to the light receiver, comparing the phase position of a reference signal corresponding to the produced transmitting light beam with the phase position of a receiving signal produced by the light receiver corresponding to the reflected part of the received light, determining the object distance on the basis of the phase difference resulting from the comparison.

9. A method according to claim 8 characterized by a linearizing of a signal corresponding to the phase difference, in dependence on a signal corresponding to the light intensity of the received light beam, and on optical parameters.

* * * * *